(12) United States Patent
Stone et al.

(10) Patent No.: US 6,491,626 B1
(45) Date of Patent: Dec. 10, 2002

(54) ARTICULATION SYSTEMS FOR POSITIONING MINIMALLY INVASIVE SURGICAL TOOLS

(75) Inventors: Corbett W. Stone, San Diego, CA (US); David G. Matsuura, Escondido, CA (US); Walter D. Gillespie, San Diego, CA (US); James F. Marino, La Jolla, CA (US)

(73) Assignee: NuVasive, San Diego, CA (US)

( * ) Notice: Subject to any disclaimer, the term of this patent is extended or adjusted under 35 U.S.C. 154(b) by 0 days.

(21) Appl. No.: 09/548,901

(22) Filed: Apr. 13, 2000

Related U.S. Application Data

(60) Provisional application No. 60/129,703, filed on Apr. 16, 1999.

(51) Int. Cl.[7] ............................... A61B 1/00; F16D 1/00
(52) U.S. Cl. ..................... 600/141; 600/139; 403/291
(58) Field of Search ................................. 600/140, 141; 403/220, 291, 52

(56) References Cited

U.S. PATENT DOCUMENTS

| | | | |
|---|---|---|---|
| 4,646,738 A | 3/1987 | Trott | |
| 4,834,069 A | 5/1989 | Umeda | 128/4 |
| 5,143,475 A | 9/1992 | Chikama | 403/291 |
| 5,178,129 A * | 1/1993 | Chikama et al. | 138/120 |
| 5,322,505 A | 6/1994 | Krause et al. | 604/24 |
| 5,454,827 A | 10/1995 | Aust et al. | 606/170 |
| 5,681,263 A * | 10/1997 | Flesch | 600/139 |
| 5,749,828 A * | 5/1998 | Solomon et al. | 600/139 |
| 5,807,241 A * | 9/1998 | Heimberger | 600/139 |
| 6,364,828 B1 * | 4/2002 | Yeung et al. | 174/68.3 |

* cited by examiner

*Primary Examiner*—Gary Jackson
(74) *Attorney, Agent, or Firm*—Jonathan Spangler

(57) ABSTRACT

An articulator for positioning a tool during a surgical procedure, comprising: a longitudinally extending body; a plurality of transverse grooves extending inwardly from opposite lateral sides of the longitudinally extending body; and a plurality of recesses extending inwardly from the opposite lateral sides of the longitudinally extending body, the plurality of recesses defining an articulation control wire lumen and a tool control wire lumen, and wherein the tool control lumen is disposed collinear with a neutral bending axis of the articulator.

35 Claims, 15 Drawing Sheets

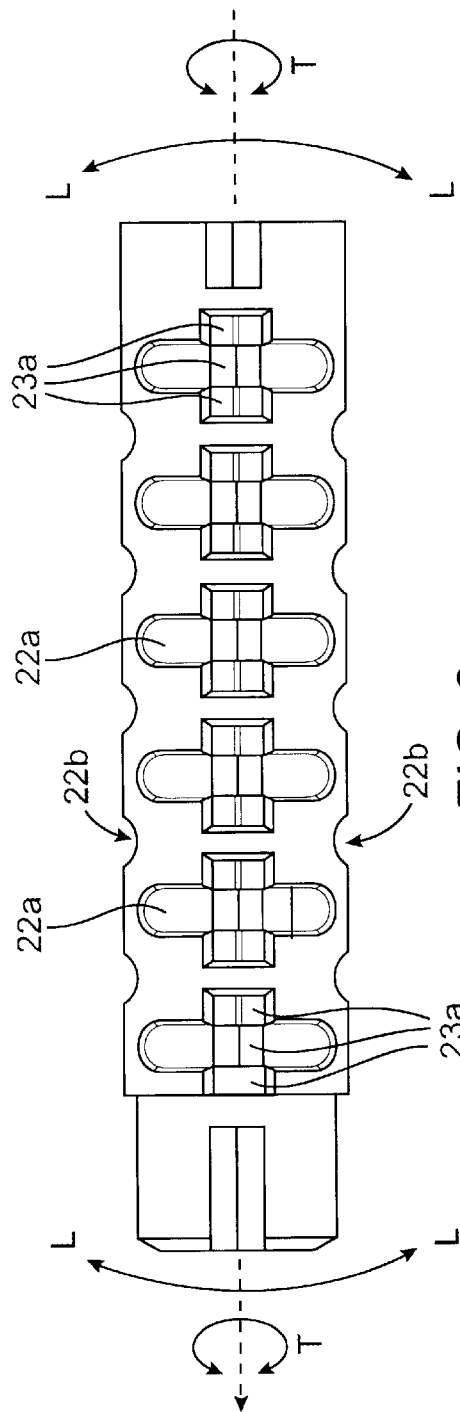
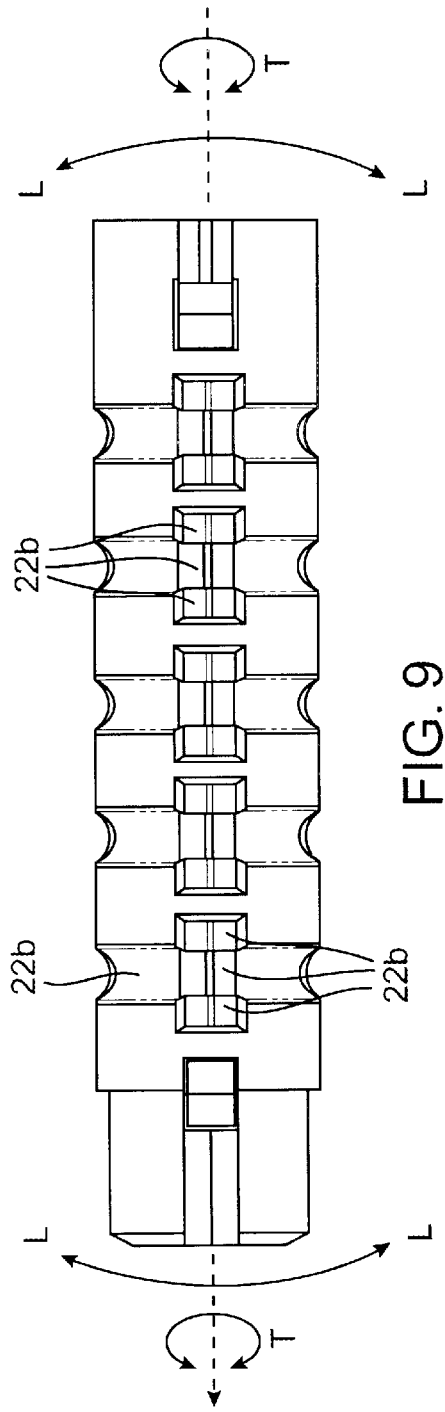

ARTICULATION SYSTEMS FOR POSITIONING MINIMALLY INVASIVE SURGICAL TOOLS

CROSS-REFERENCES TO RELATED APPLICATIONS

The present application is a regular patent application of and claims the benefit of priority from U.S. Provisional Patent Application Serial No. 60/129,703 filed Apr. 16, 1999, the full disclosure of which is incorporated herein by reference.

TECHNICAL FIELD

The present invention relates to surgical articulators.

BACKGROUND OF THE INVENTION

The effectiveness of various therapeutic tools such as graspers, punches, curettes, and scrapers which are used to manipulate tissue during minimally invasive surgical procedures can be enhanced with the addition of an articulating segment (herein, an "articulator") mounted between the distal end of a positioning rod and the base of the tool.

Accordingly, systems have been devised for providing controllable articulation of such therapeutic tools in one or more directions when the therapeutic tool is mounted to the distal end of the delivery rod. Such articulators are typically steered (ie: deflected) to position the therapeutic tool adjacent to the desired tissue by means of control rods, cables or other actuation mechanisms located in a hand piece at a proximal end of the positioning rod.

Traditional means for providing articulation include devices comprising a multiplicity of annular rings which are interlinked together to form pivots which allow for flexure of the articulator assembly. Specifically, these pivots are oriented in a manner which creates one or more preferential bending planes. One drawback of this type of articulator design is that it can lack sufficient positional stability for precision tissue manipulation when mounted to the distal end of a positioning rod.

For example, modes of instability of such devices include torsional instability about its longitudinal axis (especially when deflected, as the moment arm increases with increased articulation), radial instability about the longitudinal axis, (including lateral instability in directions perpendicular to the preferred bending plane of the articulator), and axial instability along the longitudinal axis of the articulator body. Moreover, such annular ring designs are typically machined from separate stainless steel pieces which must be assembled to form the articulator assembly, with high material and labor costs.

In a number of existing systems, a first control wire is used to control the articulation of the device, (such as for deflecting the angle of a scraper or a pair of forceps from the longitudinal axis of the positioning rod), and a second control wire is used to control the operation of the device, (such as for opening and closing the jaws of a pair of forceps).

A common problem of such existing systems is "crosstalk" in which attempts to control the degree of articulation by displacing the device's articulation control wire results in displacement of the tool control wire, which results in tool operation, or vice versa. Consequently, when operating forceps for example, the forceps jaws will tend either to open or to close as the angle of articulation is varied. Conversely, when attempting to open or close the forceps jaws, the angle of articulation of the forceps will tend to change. This "crosstalk" problem is undesirable since the surgeon may simply desire to open and close the forceps (thus grasping targeted tissue) while the forceps remain in a constant deflected position. Similarly, the surgeon may simply wish to articulate the angle of the forceps without either opening or closing their jaws, (such as when first approaching the target tissue).

In existing systems, articulators are typically constructed from soft plastics such as low durometer polyeurathanes in order to have sufficient bending flexibility. Unfortunately, the use of such soft plastics results in significant losses to the device's positional stability. Specifically, the articulator tends to compress in the axial direction when the articulation control wire is tensioned to deflect the distal end of the articulator. Such unwanted axial compression results in positioning inaccuracies which further exacerbates crosstalk problems.

SUMMARY OF THE INVENTION

The present invention provides an articulation system for positioning various surgical tools during surgical procedures, and is especially useful in positioning surgical tools in minimally invasive surgical procedures.

In a preferred aspect, the present invention provides a controllable articulator which is preferably mounted between the distal end of a positioning rod and the base of the surgical tool. An advantage of the present invention is that the positioning rod (with the articulator and surgical tool attached thereon at its distal end) may be introduced into a patient through a percutaneous cannula in a minimally invasive surgical procedure. Accordingly, the present invention is well suited for use in any manner of a minimally invasive surgery, including, but not limited to, arthroscopy and minimally invasive spinal surgery.

In a first aspect, the present articulator system comprises a longitudinally extending body which may preferably be integrally formed from a single piece or block of material. For example, the present articulator may preferably be formed by injection molding or formed by Steriolithography (SLA). An advantage of the present articulator being integrally formed from a single piece of material is that labor and material costs are substantially reduced (as compared to existing articulation systems which must be assembled piece by piece from a number of separate components).

In one preferred aspect, the present articulator is fabricated from a relatively rigid and strong thermoplastic material, for example acetal. As will be explained, the novel shape and characteristics of the present articulator system allows it to exhibit excellent bending flexibility in a preferred bending plane, yet still be constructed of a sufficiently hard material to prevent axial compression, radial deflection in planes other than the preferred bending plane (including lateral deflection in a plane perpendicular to the preferred bending plane) and torsional deflection about the central axis of the articulator body. As such, the positioning of the present articulator can be very precisely controlled through various degrees of deflection.

The novel shape of the present articulator also offers many advantages in its fabrication. For example, when injection molding the present invention, a tool control wire lumen and an articulation control wire lumen can be formed without "core pins" being required in mold shut-offs as is typically necessary to carve out separate actuator wire and control wire lumens as a hot plastic is initially flowed through the mold.

An advantage of not requiring such "core pins" when injection molding the present articulator is that the present articulator can be fabricated to very small dimensions. When attempting to form small lumens in existing injection molded parts, the size of the lumens are typically limited to the minimum diameter and length of a core pin which can be passed through the mold. This is due to the fact that it is not possible to use a core pin which is too thin since its structure will be affected by the hot plastic surrounding it during the molding process.

In contrast, the present articulator can be formed within interlocking 2-piece mold shut-offs without requiring the insertion of core pins into the mold to carve out lumens for either of the articulation or tool(i.e.: actuation) control wires.

The present articulator preferably comprises a longitudinally extending body, having a plurality of transverse grooves extending inwardly from opposite lateral sides of the longitudinally extending body. The transverse grooves preferably extend inwardly from each of the opposite lateral sides of the device in an alternating manner along the length of the longitudinally extending body. As such, the alternating nature of the transverse grooves enables the articulator to be highly flexible in a single preferred bending plane, as will be explained.

Preferably, the transverse grooves extend farther into the articulator body from one side of the articulator than from the other. In such a case, the longer grooves will be disposed on an inner bending surface of the articulator and will be compressed together as the articulator deflects in a preferred bending plane and the shorter grooves will be disposed on an outer bending surface of the articulator and will spread apart to offer stress relief as the articulator is deflected. As will be explained, the depth and spacing of the transverse grooves will define a neutral bending axis through the articulator body.

The articulator body preferably further comprises a plurality of recesses extending inwardly from the opposite sides in an alternating manner along the length of the longitudinally extending body. Such a plurality of recesses projecting inwardly from the opposite sides of the articulator body together preferably define both an articulation control wire lumen and a tool control wire lumen.

Preferably, the tool control lumen is disposed collinear with the neutral bending axis of the articulator. An important advantage of having the tool control wire, (which is received in the tool control wire lumen), collinear with a neutral bending axis of the articulator is that the potential for crosstalk is eliminated. This is due to the fact that deflection of the articulator about its neutral bending axis will neither cause tension nor compression in the tool control wire. As such, the tool control may, for example, be used to open and close teeth on a gripping device unaffected by deflection of the articulator caused by tensioning or compressing the articulation control wire (disposed in the articulation control wire lumen running parallel to the tool control wire). As such, the surgeon may use forceps positioned at the distal end of the articulator to grasp tissue when the articulator is in an articulated (i.e.: deflected) position and then apply a load to the articulator by pulling on the tissue. By positioning the forceps jaw opening control wire along the neutral bending axis of the articulator, the articulator will maintain the deflected position and will not straighten out as the forceps jaw control wire slides through the articulator to open or close the forceps. Correspondingly, another advantage of the present invention is that by placing the tool control wire collinear with the neutral axis, axial loads on the tool control wire do not cause unintended deflections of the articulator.

The transverse grooves which extend partially across the longitudinally extending body in an alternating fashion offer the advantage of significant bending flexibility in a preferred bending plane. In a preferred aspect of the invention, the innermost ends of the transverse grooves are rounded to further relieve bending stresses when the articulator is deflected.

In one preferred aspect of the invention, the transverse grooves are spaced evenly apart along the length of the articulator. As such, the articulator bends with a uniform curvature along its length. In other preferred aspects of the invention, the spacing between the transverse grooves is varied such that the articulator bends with different arcs of curvature along its length. For example, the transverse grooves can be spaced closer together at the distal end of the articulator such that maximum deflection curvature occurs at the distal end of the articulator.

The novel shape of the present articulator makes it highly flexible in a preferred bending plane, yet highly resistant to loads in other directions. Specifically, the present articulator is resistant to lateral loads, (perpendicular to the plane of deflection), torsional loads, and axial loads, or any combination thereof.

In a preferred aspect, free floating tension/compression sleeves may optionally be placed in the tool and articulation control wire lumens over the tool and articulation control wires thus preventing the actuators from sliding thereby improving control feel by imparting further rigidity to the articulator. Preferably, such sleeves can be made of low coefficient of friction materials thereby reducing excessive actuation friction.

In another aspect of the present invention, the plurality of recesses projecting inwardly from the top and bottom of the device together define a large central lumen which is adapted to receive both the articulation control wire and the tool control wire therethrough. Such a large central lumen may optionally have a keyhole shape (in cross section) to assist in holding the tool control wire coincident with the neutral bending axis of the articulator, as will be explained.

In another aspect of the present invention, the recesses which extend inwardly from the opposite sides of the articulator body are eliminated. Instead, the articulation control wire lumen is formed as a series of spaced apart cylinders which pass between the transverse grooves extending from one side of the articulator body. The articulation control wire lumen thus formed opens fully into the transverse grooves which extend into one side of the articulator body. In this aspect of the invention, the tool control wire lumen (which is disposed collinear with the neutral bending axis) opens directly into the innermost ends of the transverse grooves which extend inwardly from both opposite sides of the articulator body.

BRIEF DESCRIPTION OF THE DRAWINGS

FIG. 8 is a top plan view of the articulator of FIG. 1.

FIG. 9 is a bottom plan view of the articulator of FIG. 1.

DESCRIPTION OF THE PREFERRED EMBODIMENTS

The present invention provides an articulation system which is adapted to be mounted between the distal end of a positioning rod and the base of a surgical tool such as a scraper, a curette, forceps, graspers or scissors. The present articulator is designed to bend within a preferred bending plane under the influence of tension from an articulation control wire passing therethrough. The preferred bending characteristics of the present articulator facilitates the accurate positioning of the various surgical tools which may be mounted on its distal end. As such, the present articulation system is particularly well suited for minimally invasive surgical applications in which a cannula is first introduced into the patient's body and the surgical tool (mounted to the articulator which is then mounted to a positioning rod) is then introduced through the cannula. After approaching a selected target tissue, the surgical tool and the articulator can be advanced to protrude out of the distal end of the cannula such that the articulator can then be deflected to direct the surgical tool into orientations which are not collinear with a cental axis of either the positioning rod or the cannula.

Figure 1:
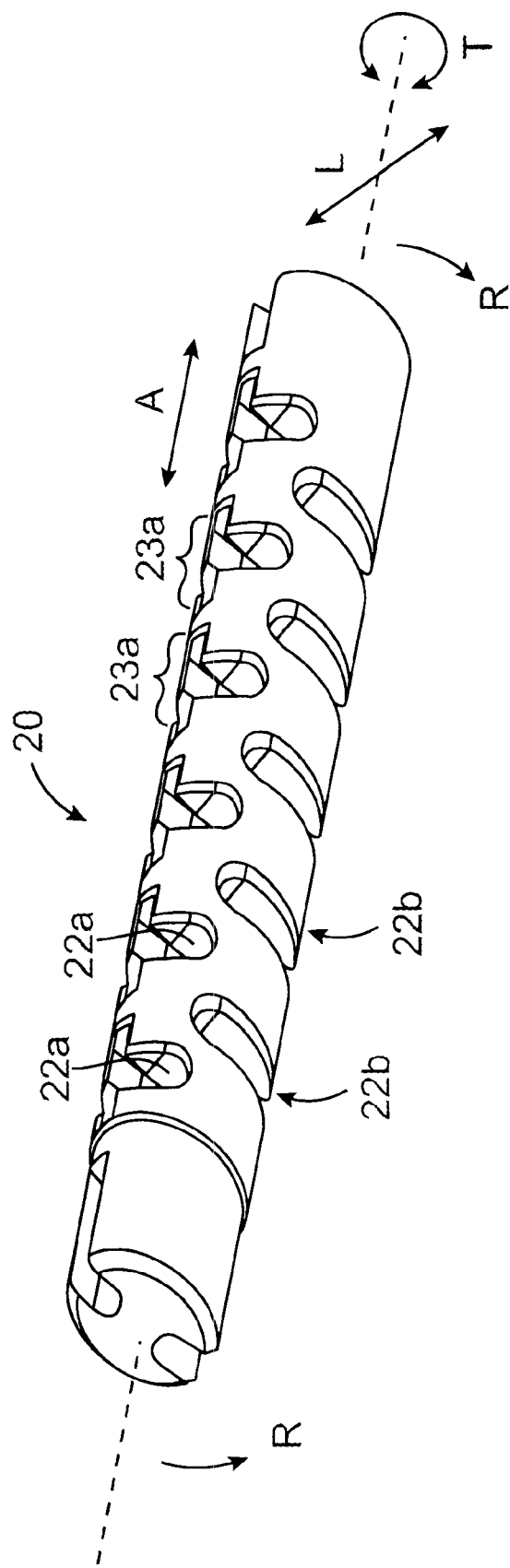
FIG. 1 is a perspective view of an articulator according to the present invention.

Referring to FIG. 1, an articulator 20 is provided. Articulator 20 is preferably monolithically fabricated from a single, integral piece of high density thermoplastic such as acetal. The novel shape of articulator 20 permits easy, highly flexible bending in direction R, (due to the presence of transverse grooves 22A and 22B which provide stress relief), yet prevents lateral bending in directions L, and also resists axial compression in direction A and torsional bending in direction T.

Figure 17:
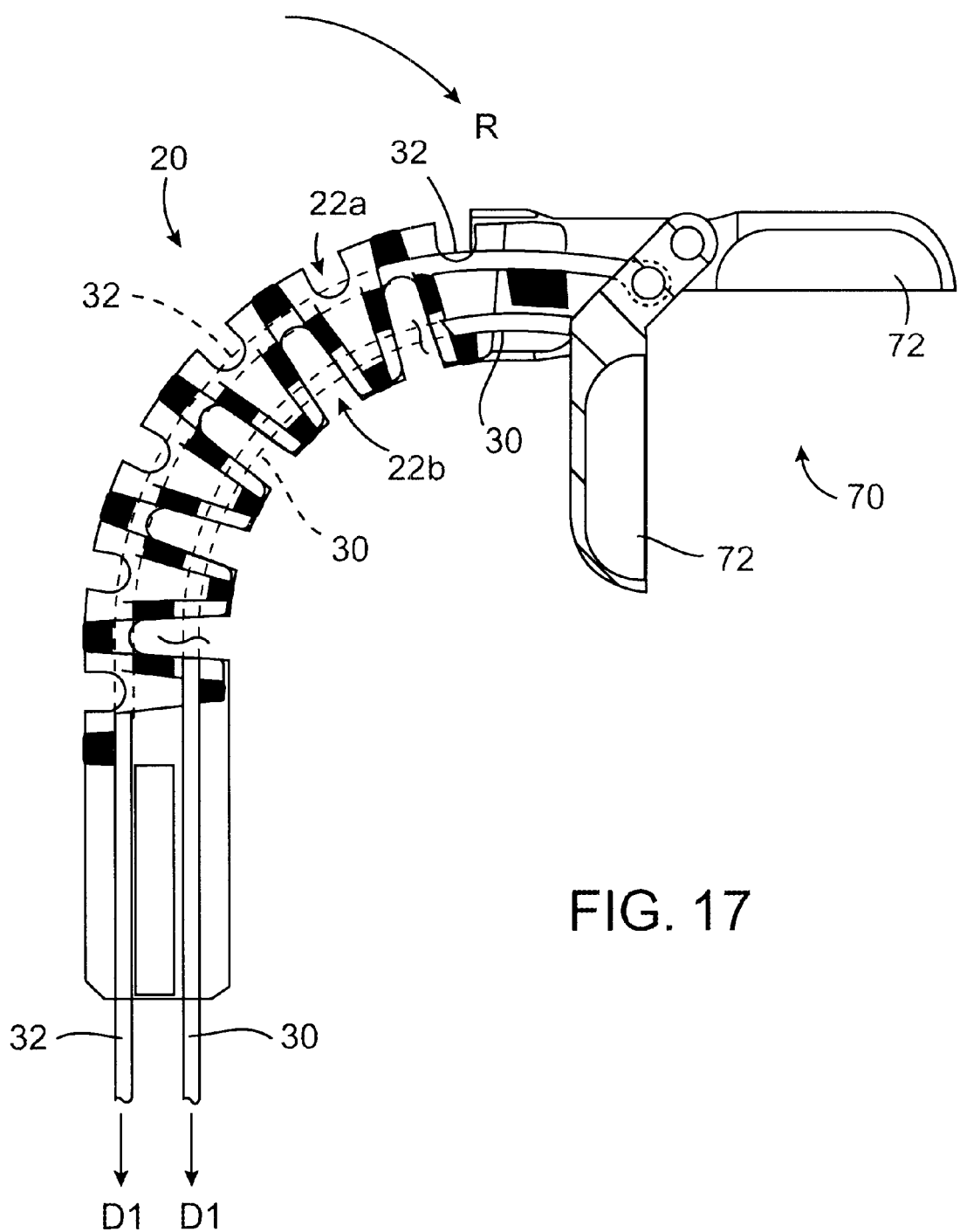
FIG. 17 is a sectional side view of the articulator of FIG. 1 in a deflected position.

Referring to FIG. 2, the internal structure of articulator 20 can be seen in more detail. FIG. 2 shows one half of the articulator. As can be seen, a plurality of transverse grooves 22A and 22B extend inwardly into opposite lateral sides (illustrated herein as the top and bottom of articulator 20). As can be seen in FIG. 3, grooves 22B extend further inwardly (i.e.: laterally across) articulator 20 than grooves 22A. Accordingly, articulator 20 is adapted to flex in direction R as shown in FIG. 17, with grooves 22B narrowing as the articulator is bent in direction R while grooves 22A spread apart to provide stress relief as the articulator bends.

The "preferred bending plane" for articulator 20 is shown as "BP" in FIG. 4. Specifically, when actuated, articulator 20 is adapted to preferentially bend in direction R in preferred bending plane BP).

Figure 2A:
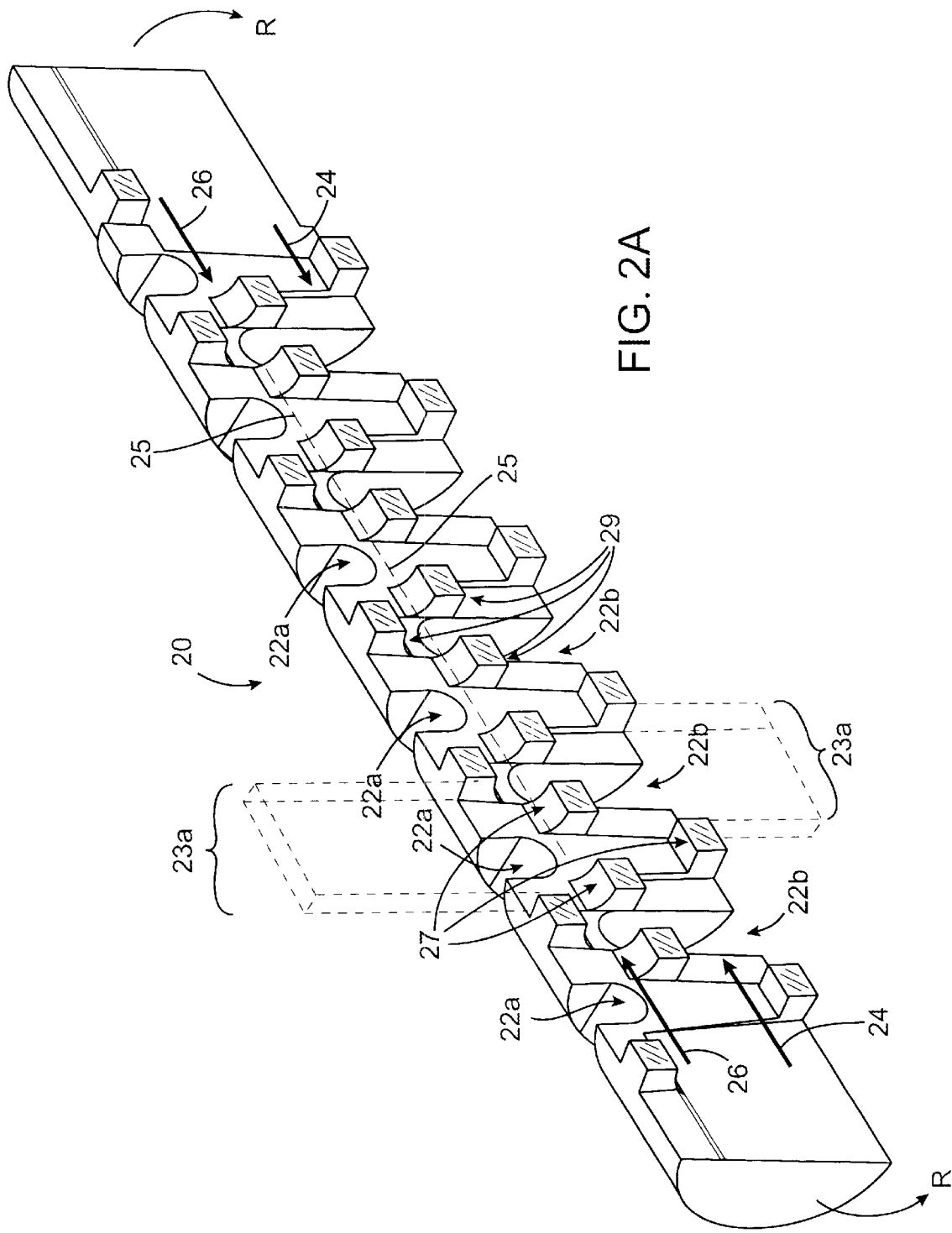
FIG. 2A is a sectional view showing one half of the articulator of FIG. 1.
Figure 2B:
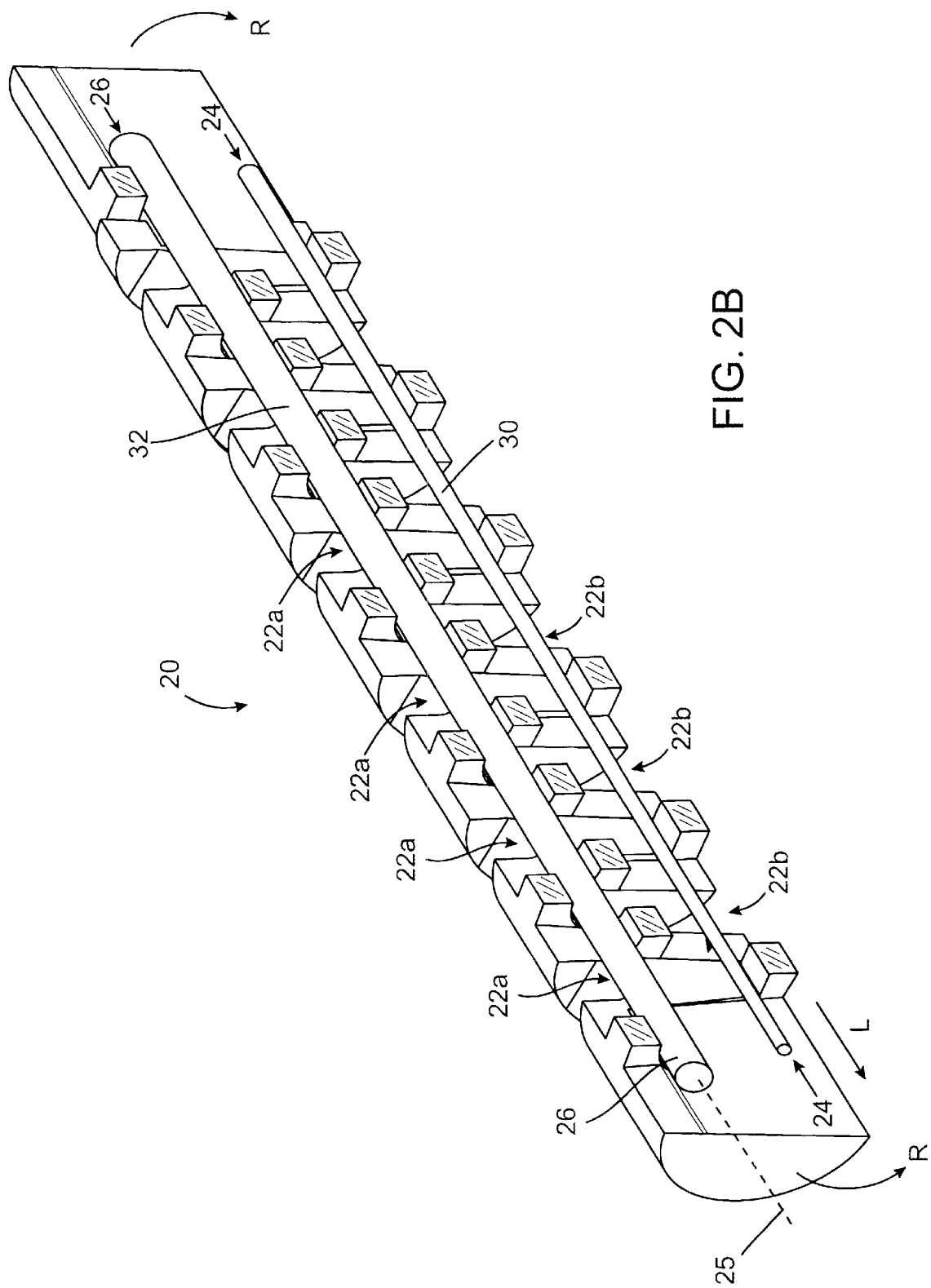
FIG. 2B corresponds to FIG. 2A, further showing the tool and articulation control wires.
Figures 3, 4:
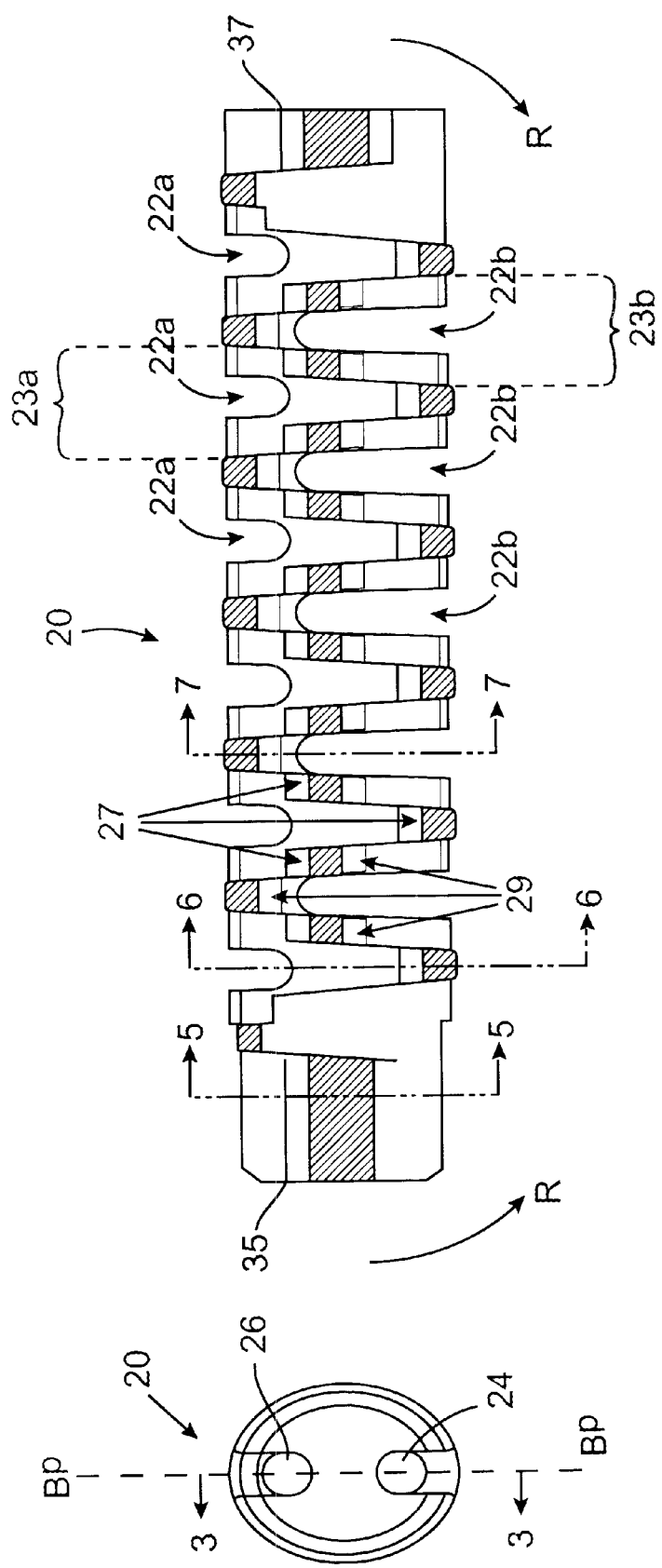
FIG. 3 is a side sectional view corresponding to FIG. 2A.
FIG. 4 is an end view corresponding to FIG. 3.
Figure 7:
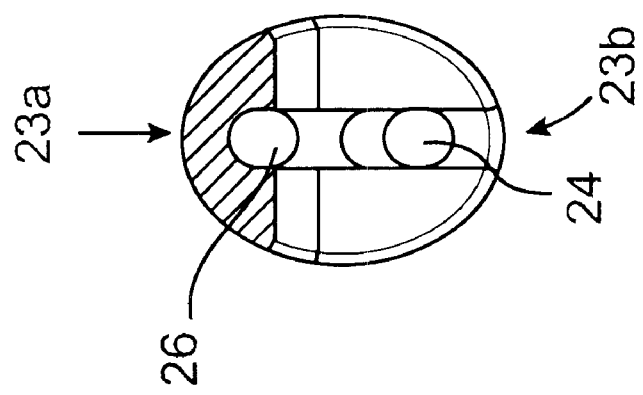
FIG. 7 is a sectional view taken along line 7—7 in FIG. 3.
Figure 6:
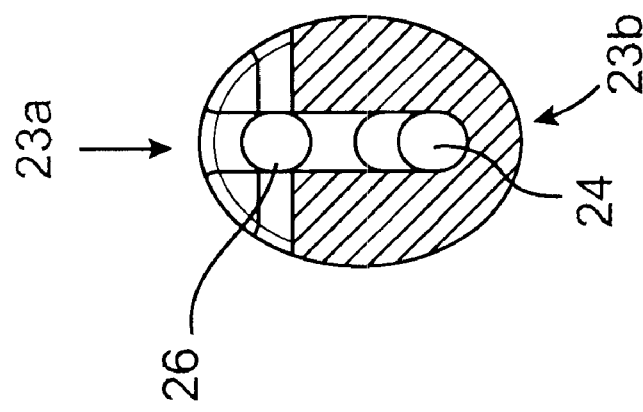
FIG. 6 is a sectional view taken along line 6—6 in FIG. 3.
Figure 5:
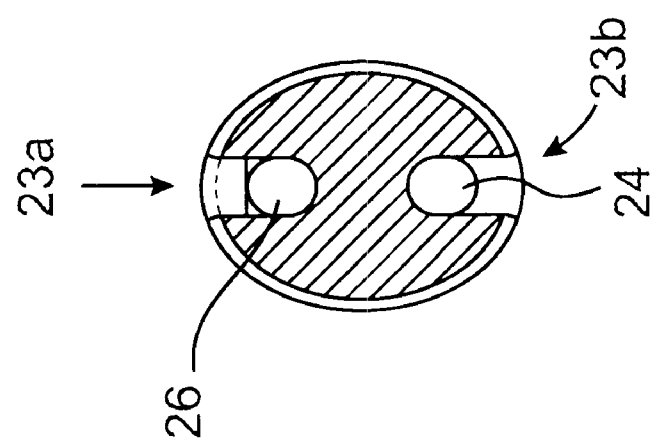
FIG. 5 is a sectional view taken along line 5—5 in FIG. 3.

As seen in FIGS. 2A and 3, a plurality of recesses 23A and 23B extend inwardly from the opposite top and bottom sides of articulator 20. Recesses 23A and 23B extend inwardly such that their innermost ends 27 and 29, overlap, so as to define an actuator control wire lumen 24 and a tool control wire lumen 26 through articulator 20 as shown. As seen in FIG. 2B, an actuation control wire 30 is slidably received within actuator control wire lumen 24 and a tool control wire 32 is slidably received within tool control wire lumen 26.

An advantage of recesses 23A and 23B extending inwardly with their innermost ends 27 and 27 overlapping as shown (to form lumens 24 and 26) is that it is possible to injection mold articulator 20 from a single monolithic piece of thermoplastic or other suitable material. As such, recesses 23A and 23B can be formed by similar shaped protrusions disposed on opposite halves of the mold shut-offs. As such, lumens 24 and 26 are formed to extend through articulator 20 without requiring the insertion of any core pins into an injection mold to first carve out such lumens. Consequently, the present articulator can be fabricated to very small dimensions since a thin core pin is not required.

When articulator control wire 30 is tensioned, (i.e.: pulled in direction D1), articulator 20 will be deflected in direction R to a position as show in FIG. 17. (For clarity, portions of wires 30 and 32 are illustrated in phantom in FIG. 17). When tool control wire 32 is tensioned, (i.e.: pulled in direction D1), control wire 32 can actuate a tool. For example, control wire 32 can be used to open jaws 72 of forceps 70.

An important aspect of the present invention is that tool control wire 32 is preferably disposed along the neutral bending axis 25 (FIG. 10A) of articulator 20. An important advantage of disposing control wire 32 collinear with neutral axis 25 is that control wire 32 will neither be tensioned nor compressed as articulator 20 deflects back and forth in direction R under the control of actuator control wire 30.

Accordingly, the angle of articulation (in direction R within the device's preferred bending plane BP) can be easily changed by either tensioning or relaxing tension on articulation control wire 30 without axially displacing tool control wire 32 (which would for example induce "crosstalk" affecting the operation of the surgical tool, such as opening or closing jaws 72 of forceps 70).

By positioning control wire 32 collinear with the neutral bending axis of articulator 20, the operation of a tool (such as forceps 70) is fully independent of operation of the controlling of the angle of articulation (in direction R) of articulator 20.

Further details of the internal structure of articulator 20 can be seen in FIGS. 4 to 7.

As can be seen in FIGS. 8 and 9, the lateral sides of articulator 20 are substantially straight when viewed from either the top or the bottom of the device. Such preferred shape of articulator 20 (i.e.: wherein grooves 22a and 22b project into the top and bottom of the device, with no similar grooves projecting into the lateral sides of the device) offers resistance to bending both in lateral directions L and torsional directions T.

Figure 10A:
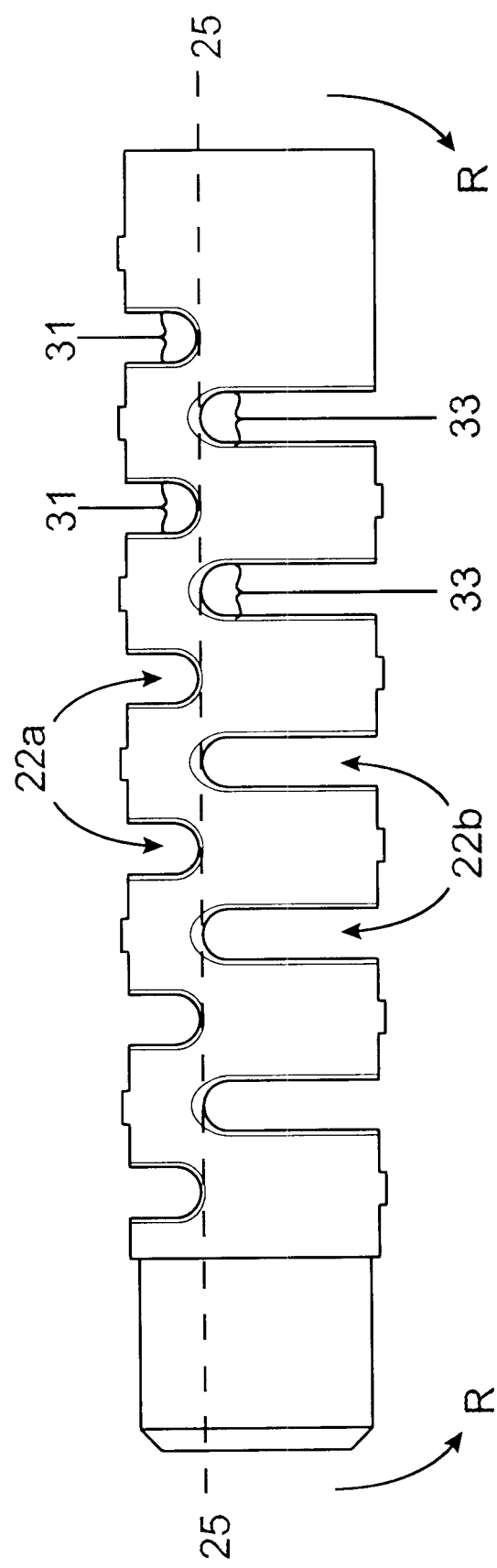
FIG. 10A is a side elevation view of the articulator of FIG. 1.

As can be seen in FIG. 10A, inner most ends 31 and 33 of grooves 22A and 22B respectively are preferably rounded to further relieve bending stresses when articulator 20 is bent in its preferred bending plane, (BP in FIG. 4), in direction R, thus enabling a high degree of flexibility in the preferred bending plane.

Figure 10B:
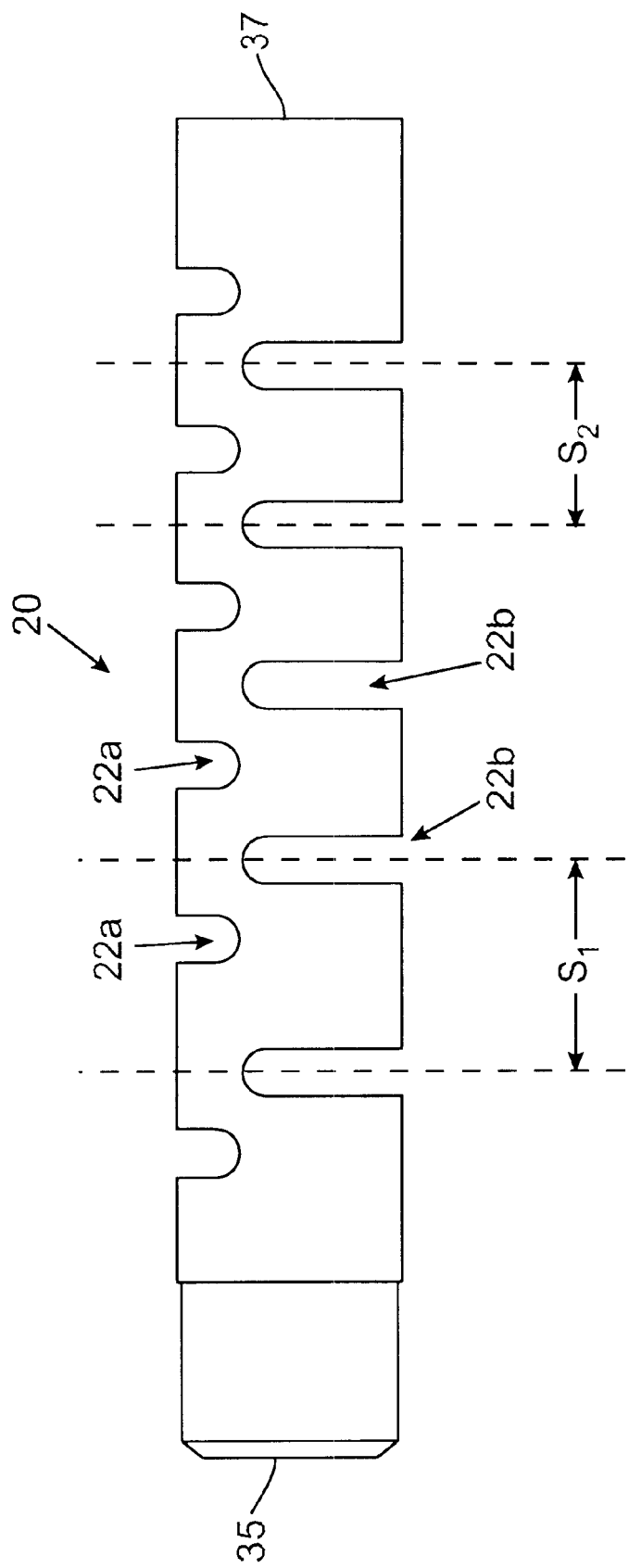
FIG. 10B is a view corresponding to FIG. 10A, but showing the spacing between adjacent transverse grooves narrowing toward one end of the articulator.

FIG. 10B shows an aspect of the invention where the spacing between adjacent grooves 22B (and 22A) is decreased from S1 to S2 towards distal end 37 of articulator 20. As such, the articulator will tend to exhibit a greater degree of curvature towards its distal end 37 as compared to its proximal end 35 when articulator control wire 30 is tensioned. Having a highly flexible distal end, the articulator of FIG. 10B is particularly well suited for accessing highly curved or branching passageways in the patient's body.

FIGS. 11A to 11D show an alternate aspect of the present articulator. Articulator 40 is shown in cross-sectional view, similar to the view of articulator 20 shown in FIG. 2A. In contrast to articulator 20, articulator 40 has a large central lumen 42 passing therethrough. Articulator 40 is similar to articulator 20 with transverse grooves 42A and 42B functioning similar to grooves 22A and 22B in articulator 20. Recesses 43A and 43B are, however, differently shaped from recesses 23A and 23B such that only one large central lumen 42 is formed through articulator 40.

Figure 11A:
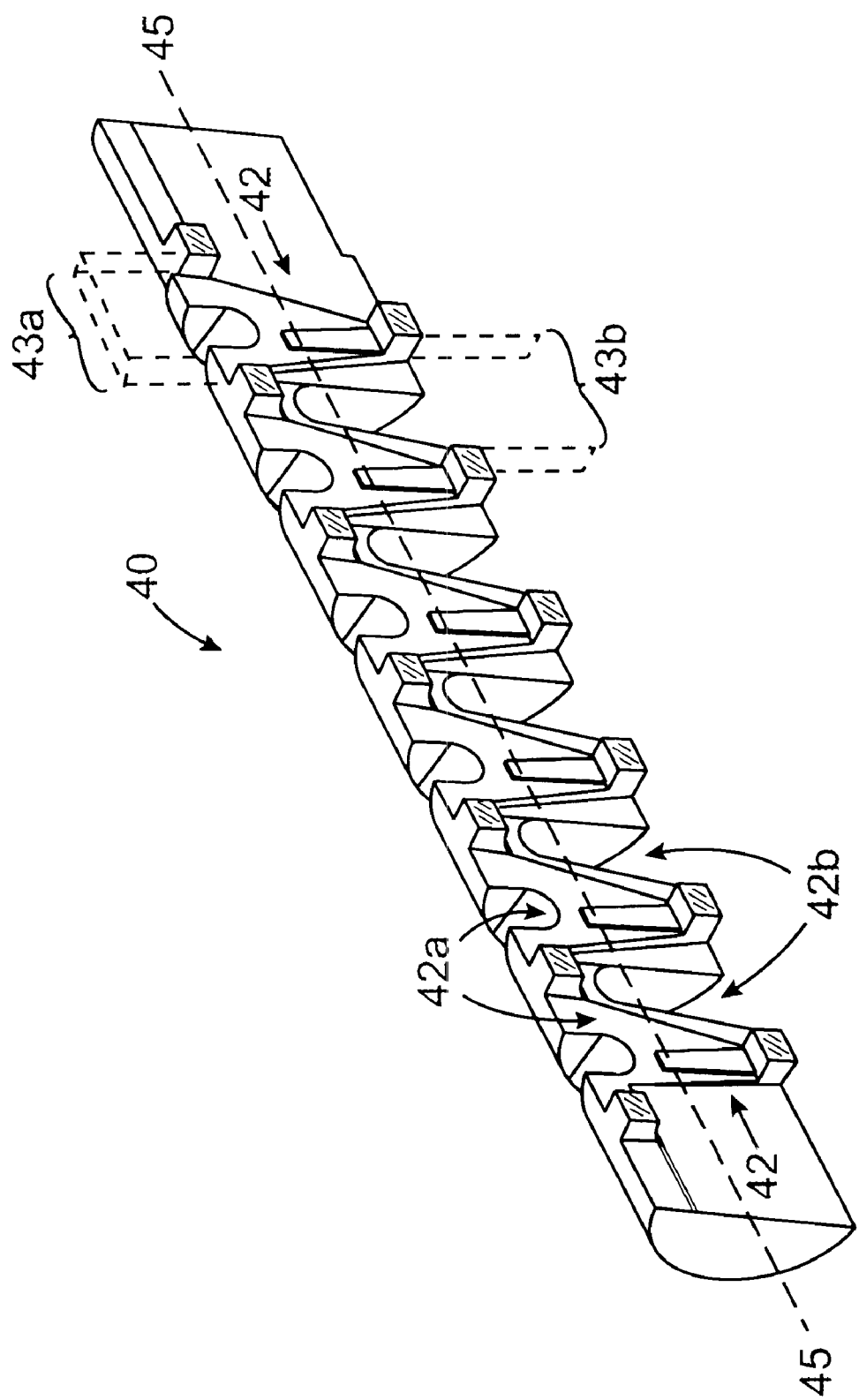
FIG. 11A is a sectional perspective view of an alternate design of an articulator according to the present invention.
Figure 11B:
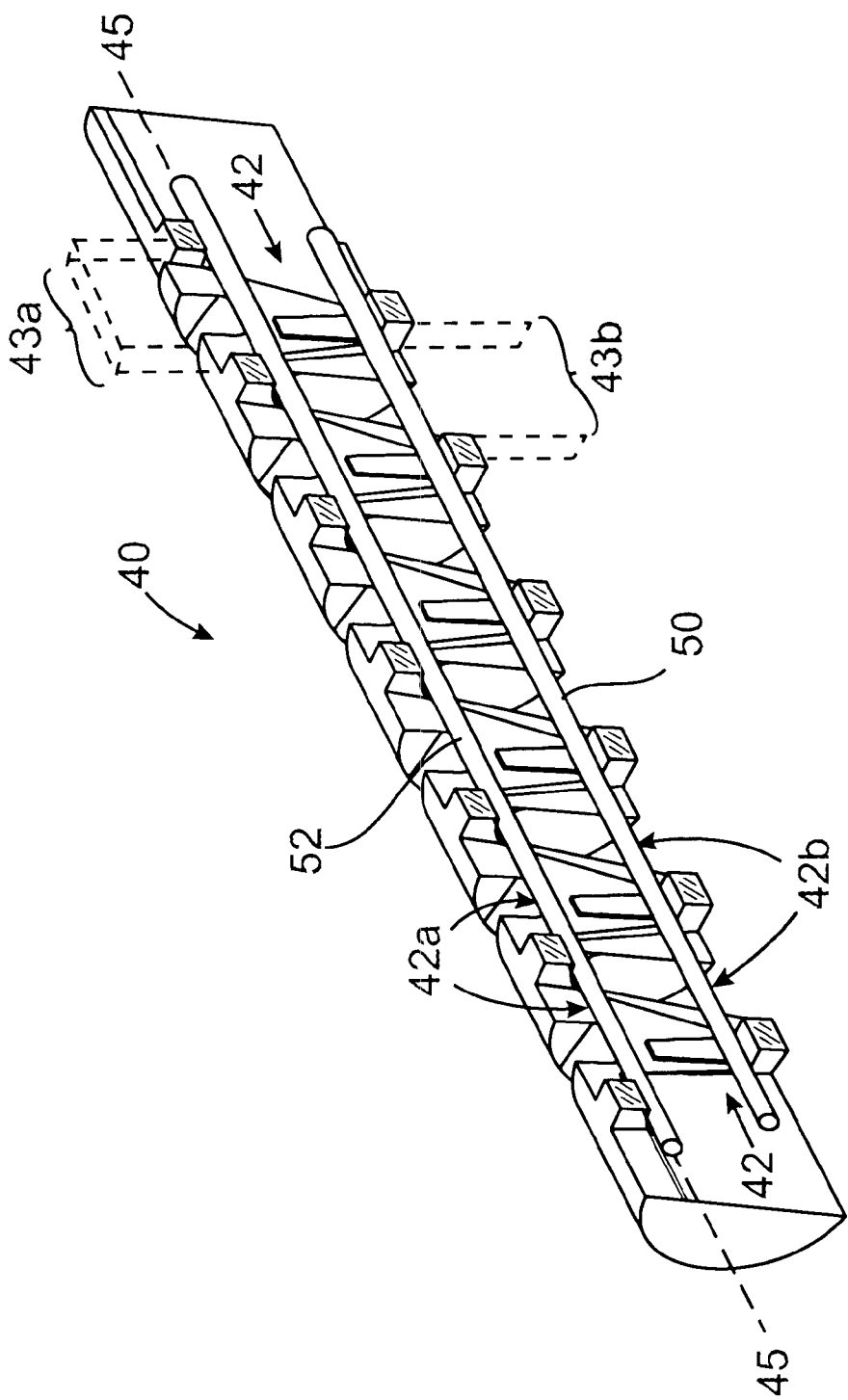
FIG. 11B is a sectional perspective view of a articulator of FIG. 11A, showing the actuator control wire and the tool control wire received together in a large central lumen.
Figure 11D:
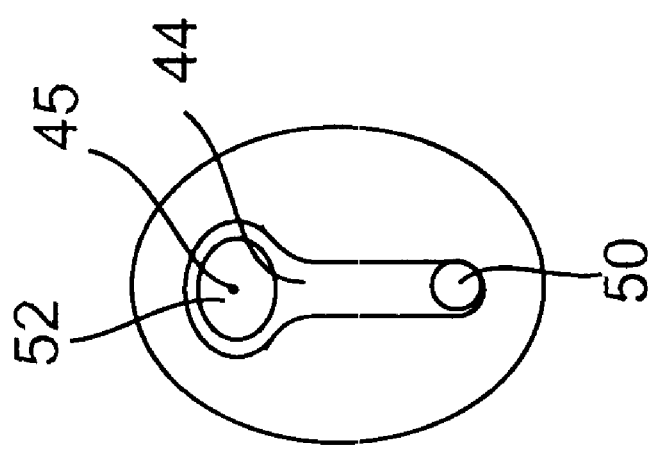
FIG. 11D is an end view corresponding to FIG. 11A, showing a single keyhole-shaped central lumen.
Figure 11C:
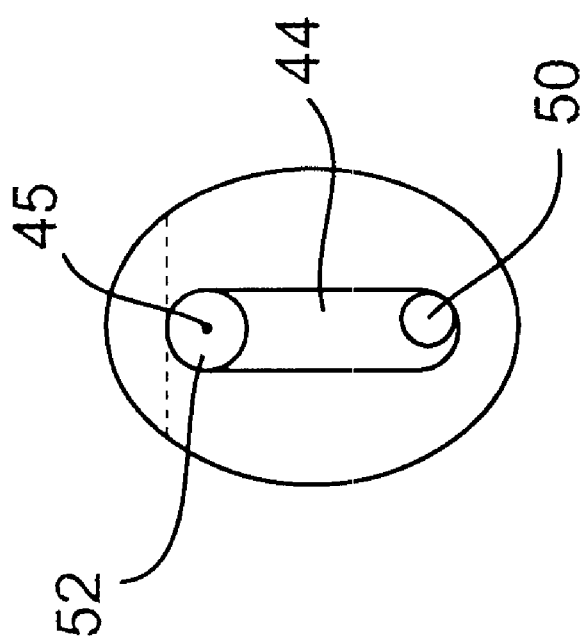
FIG. 11C is an end view corresponding to FIG. 11A, showing a single racetrack-shaped central lumen.

Lumen 42 may be a variety of shapes including racetrack-shaped as is shown in FIG. 11C or keyhole-shaped as is shown in FIG. 11D. When an articulation control wire 50, (see FIGS. 11C and 11D), is positioned in the large central lumen of FIG. 11A, tension on actuation control wire 50 will cause it to move to the contracting side of articulator 40, as shown in FIGS. 11C and 11D. A tool control wire 52 is also received within central lumen 42. Tool control wire 52 will tend to move to the opposite side of lumen 42 such that tool control wire 52 will remain disposed along the neutral bending axis 45 of articulator 40 as shown. An advantage of the keyhole shape of lumen 42 shown in FIG. 11D is that it will tend to further restrict movement of tool control wire 52 such that it remains collinear with neutral bending axis 45.

Figure 12:
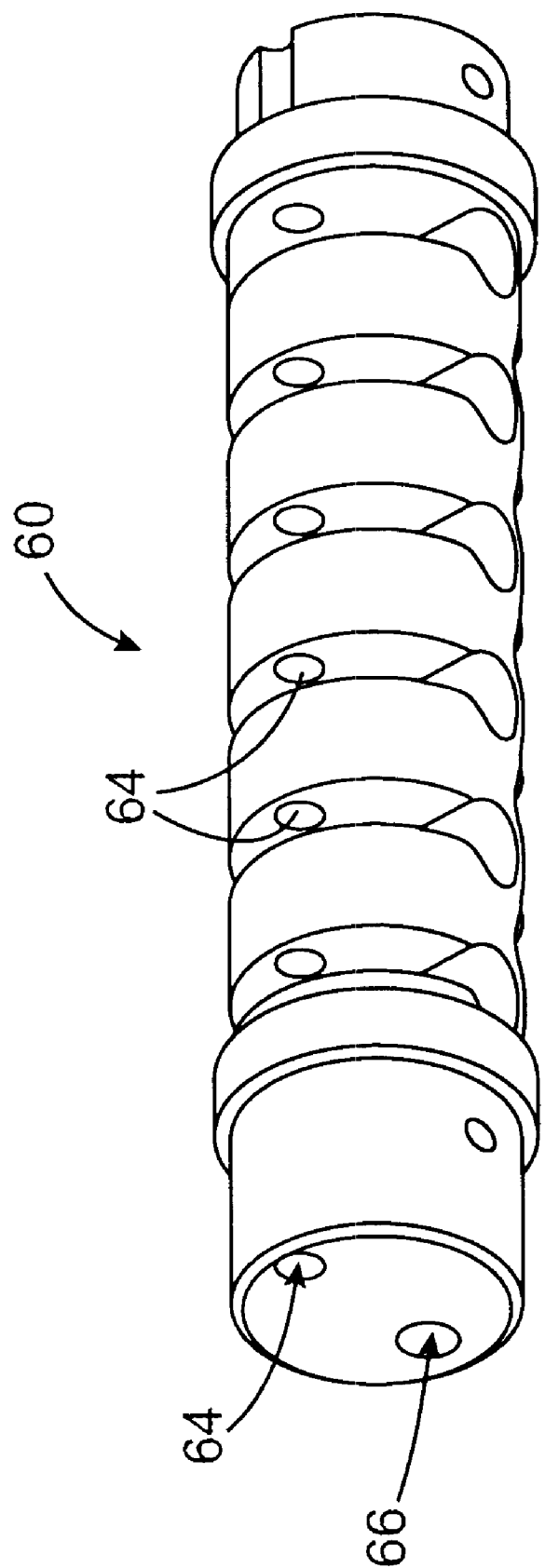
FIG. 12 is a perspective view of yet another design of an articulator according to the present invention.
Figure 14:
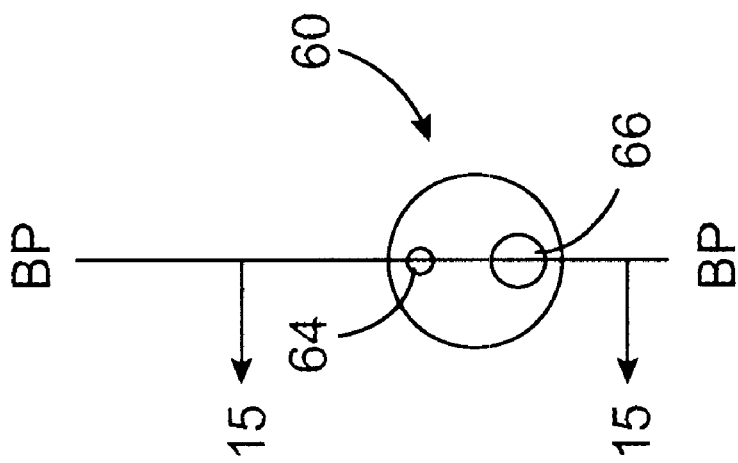
FIG. 14 is an end view of the articulator of FIG. 12.
Figure 13:
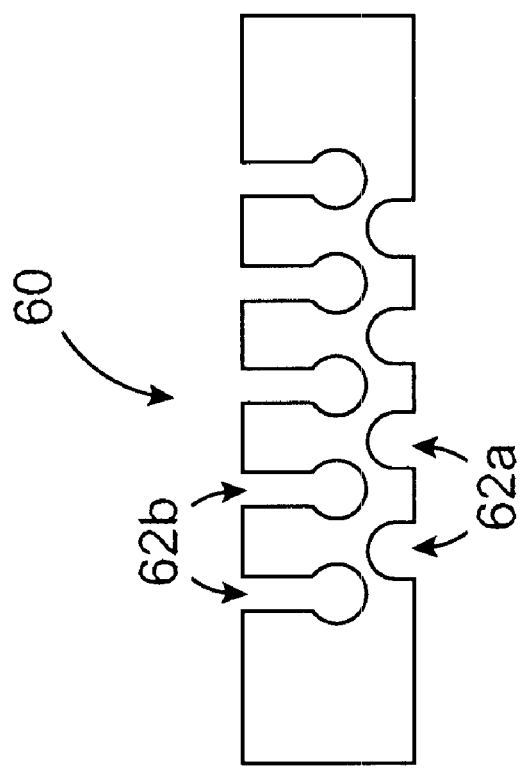
FIG. 13 is a side elevation view of the articulator of FIG. 12.
Figure 15:
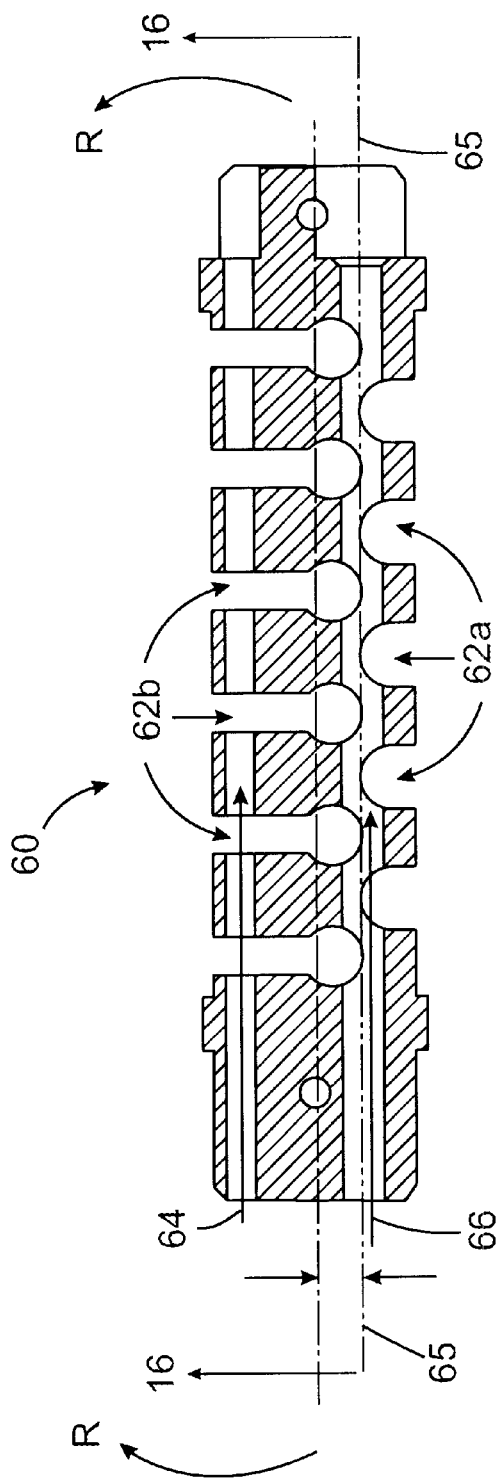
FIG. 15 is a sectional view taken along line 15—15 in FIG. 14.
Figure 16:
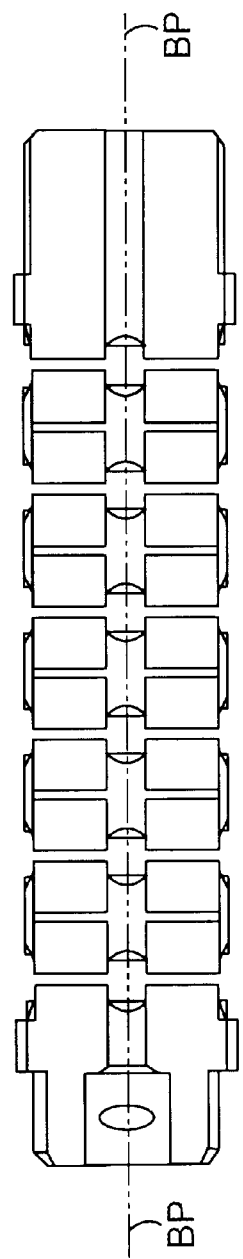
FIG. 16 is a bottom sectional view taken along line 16—16 in FIG. 15.

FIG. 12 shows another alternate aspect of the present articulator. Articulator 60 has transverse grooves 62A and 62B (which operate similar to grooves 22A and 22B in articulator 20) extending inwardly from the top and bottom of the device as shown. An articulation control wire lumen 64 and a tool control wire lumen 66 are provided as shown. Further details of lumens 64 and 66 are seen in FIGS. 15 an 16. As can be seen, articulation control wire lumen 64 passes between and opens into transverse grooves 62B and control wire lumen 66 passes through the innermost ends of both transverse grooves 62A and 62B. Tool control wire lumen 66 is preferably disposed such that a tool control wire (not shown) received therein is collinear with the neutral bending axis 65 of articulator 60. Accordingly, as the articulator is deflected, grooves 62B will tend to close as grooves 62A will tend to open. Being disposed on neutral bending axis 65, a tool control wire passing through lumen 66 will neither tend to be put under tension or compression during articulation.

Advantageously, the positioning of articulation control wire lumen 66 such that it opens both into the innermost ends of grooves 62A and 62B further reduces the bending resistance of the articulator by reducing its section modulus. As such, articulator 60 is highly flexible to bend in direction R in bending plane BP. In a preferred aspect of the present invention, a neutral axis 65 is located at the midway point between the innermost ends of transverse grooves 62A and 62B, as shown.

In further aspects of the present invention, a plurality of articulators 20, 40, or 60 can be attached together end to end. As such, the angle of articulation of the device may be substantially increased. For example, articulation for up to 360° is possible.

In other aspects of the invention, a plurality of articulators are be mounted together end to end with successive articulators being rotated 180° about a central longitudinal axis extending therethrough. When deflected, the combined articulator assembly will deflect into an S-shaped curve.

What is claimed is:

1. An articulator for positioning a tool during a surgical procedure, comprising:
    a longitudinally extending body;
    a plurality of transverse grooves extending inwardly from opposite lateral sides of the longitudinally extending body; and
    a plurality of recesses extending inwardly from the opposite lateral sides of the longitudinally extending body, the plurality of recesses defining an articulation control wire lumen and a tool control wire lumen, and wherein the tool control lumen is disposed collinear with a neutral bending axis of the articulator.

2. The articulator of claim 1, wherein the transverse grooves extend inwardly from each of the opposite lateral sides of the longitudinally extending body in an alternating manner along the length of the longitudinally extending body.

3. The articulator of claim 1, wherein the plurality of recesses extend inwardly from the opposite lateral sides of the longitudinally extending body in an alternating manner along the length of the longitudinally extending body.

4. The articulator of claim 1, wherein the transverse grooves extend further inwardly from one of the opposite lateral sides of the longitudinally extending body than from the other opposite side of the longitudinally extending body.

5. The articulator of claim 1, wherein, innermost ends of the transverse grooves are rounded.

6. The articulator of claim 1, wherein, the longitudinally extending body is generally cylindrical.

7. The articulator of claim 1, wherein, the articulator is integrally formed as a single monolithic block of material.

8. The articulator of claim 7, wherein, the articulator is injection molded.

9. The articulator of claim 7, wherein, the articulator is formed by stereolithography.

10. The articulator of claim 1, wherein, the therapeutic tool is selected from the group consisting of a scraper, a curette, a grasper, forceps, and scissors.

11. The articulator of claim 1, wherein, the plurality of transverse grooves are spaced evenly apart along the length of the longitudinally extending body.

12. The articulator of claim 1, wherein, the plurality of transverse grooves are spaced unevenly apart along the length of the longitudinally extending body.

13. The articulator of claim 12, wherein, the plurality of transverse grooves are spaced progressively closer together towards a distal end of the longitudinally extending body.

14. The articulator of claim 12, further comprising:
    a tool control wire received in the tool control wire lumen; and
    an articulator control wire received in the articulation control wire lumen.

15. An articulator for positioning a tool during a surgical procedure, comprising:
- a longitudinally extending body;
- a plurality of transverse grooves extending inwardly from opposite lateral sides of the longitudinally extending body; and
- a plurality of recesses extending inwardly from the opposite sides of the longitudinally extending body, wherein the plurality of recesses define a central control wire lumen, and wherein one side of the central control wire lumen is disposed collinear with a neutral bending axis of the articulator.

16. The articulator of claim 15, wherein the transverse grooves extend inwardly from each of the opposite lateral sides of the longitudinally extending body in an alternating manner along the length of the longitudinally extending body.

17. The articulator of claim 15, wherein the plurality of recesses extend inwardly from the opposite lateral sides of the longitudinally extending body in an alternating manner along the length of the longitudinally extending body.

18. The articulator of claim 15, wherein the transverse grooves extend further inwardly from one of the opposite lateral sides of the longitudinally extending body than from the other opposite side of the longitudinally extending body.

19. The articulator of claim 15, wherein the articulator is integrally formed as a single monolithic block of material.

20. The articulator of claim 15, wherein the central control wire lumen is dimensioned to receive both an articulation control wire and a tool control wire therethrough.

21. The articulator of claim 15, wherein the central control wire lumen has a racetrack-shaped cross section.

22. The articulator of claim 15, wherein the central control wire lumen has a keyhole-shaped cross section.

23. An articulator for positioning a tool during a surgical procedure, comprising:
- a longitudinally extending body;
- a plurality of transverse grooves extending inwardly from opposite sides of the longitudinally extending body;
- a tool control wire lumen extending longitudinally through the longitudinally extending body, the tool control wire lumen being collinear with a neutral bending axis of the articulator; and
- an articulation control wire lumen disposed parallel to the tool control wire lumen.

24. The articulator of claim 23, wherein the transverse grooves extend inwardly from each of the opposite lateral sides of the longitudinally extending body in an alternating manner along the length of the longitudinally extending body.

25. The articulator of claim 23, wherein the plurality of recesses extend inwardly from the opposite lateral sides of the longitudinally extending body in an alternating manner along the length of the longitudinally extending body.

26. The articulator of claim 23, wherein the transverse grooves extend further inwardly from one of the opposite lateral sides of the longitudinally extending body than from the other opposite side of the longitudinally extending body.

27. The articulator of claim 23, wherein the articulator is integrally formed as a single monolithic block of material.

28. The articulator of claim 27, wherein, the articulator is injection molded.

29. The articulator of claim 27, wherein, the articulator is formed by steriolithography.

30. The articulator of claim 23, wherein, the therapeutic tool is selected from the group consisting of a scraper, a curette, a grasper, forceps, and scissors.

31. The articulator of claim 23, further comprising:
- a tool control wire received in the tool control wire lumen; and
- an articulator control wire received in the articulation control wire lumen.

32. The articulator of claim 23, wherein, the tool control wire lumen is dimensioned to open into innermost ends of the transverse grooves extending inwardly from each of the opposite lateral sides.

33. The articulator of claim 32, wherein, the neutral bending axis passes mid-way between innermost ends of opposite transverse grooves.

34. The articulator of claim 23, wherein, the articulation control wire lumen passes through the transverse grooves extending from only one side of the longitudinally extending body.

35. The articulator of claim 23, wherein, the innermost ends of the transverse grooves extending from the opposite lateral sides extend past one another.

* * * * *